United States Patent [19]
Brinton, Jr. et al.

[11] Patent Number: 5,336,490
[45] Date of Patent: Aug. 9, 1994

[54] HAEMOPHILUS INFLUENZAE PILUS VACCINES

[75] Inventors: Charles C. Brinton, Jr., Export; Sam C. To, Pittsburgh, both of Pa.

[73] Assignee: Bactex, Inc., Pittsburgh, Pa.

[21] Appl. No.: 767,479

[22] Filed: Sep. 30, 1991

Related U.S. Application Data

[63] Continuation of Ser. No. 207,767, Jun. 16, 1988, abandoned.

[51] Int. Cl.⁵ .............................................. A61K 39/02
[52] U.S. Cl. .............................. 424/242.1; 424/256.1
[58] Field of Search .......................... 424/92, 88, 93 D
[56] References Cited

U.S. PATENT DOCUMENTS 4,681,762  7/1987  Oesdrger ............................ 424/92

OTHER PUBLICATIONS

Pichichero et al., The Lancet, pp. 960–962, Oct. 30, 1982.

Primary Examiner—Michael G. Wityshyn
Assistant Examiner—Abdel A. Mohamed
Attorney, Agent, or Firm—Omri M. Behr; Matthew J. McDonald

[57] ABSTRACT

There is provided a vaccine composition for protecting subjects against infections caused by piliated *Haemophilus influenzae* organisms which comprises a pharmaceutically acceptable carrier and whole *H. influenzae* pili, designated vaccine pili, previously separated from other *H. influenzae* components, in an amount capable of raising the antibody level of the subject to a level sufficient to provide such protection said vaccine comprising pili of at least one type selected from a group of pili types designated LKP1 through LKP8 said vaccine pili being agglutinable by anti sera derived from pili derived from organisms of at least one strain of one of the following said types. Methods of utilizing said vaccines are also provided.

8 Claims, 4 Drawing Sheets

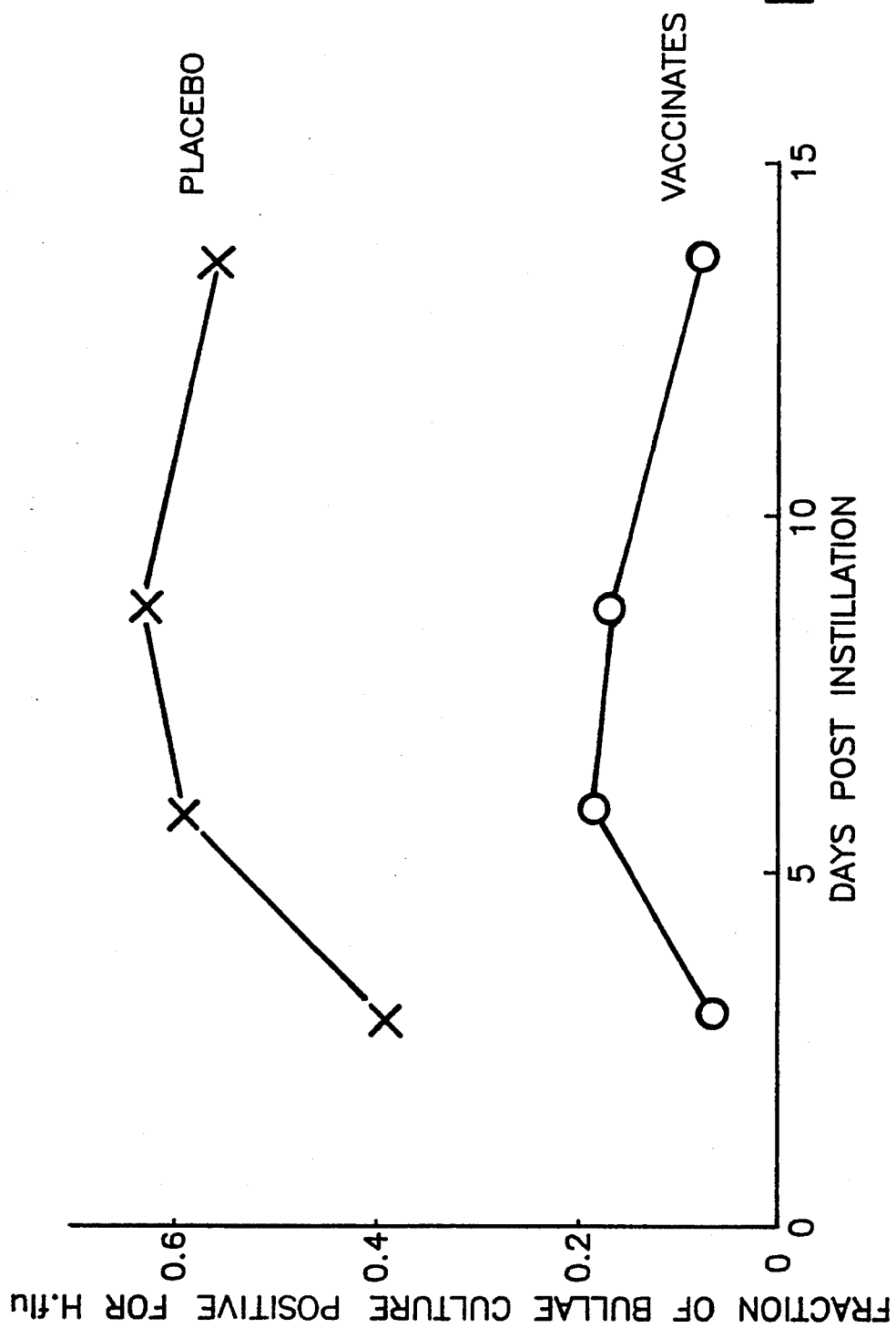

HAEMOPHILUS INFLUENZAE PILUS VACCINES

This application is a continuation, of application Ser. No. 207,767, filed Jun. 16, 1988, now abandoned.

BACKGROUND OF THE INVENTION

*H.influenzae*, a strict human pathogen, causes widespread and serious disease in both pediatric human populations (infants and children) and in adults and elderly. Pediatric diseases include mucosal surface diseases such as middle ear infections as well as invasive diseases such as meningitis, epiglottitis, septic arthritis and cellulitis. These diseases are leading causes of deafness and mental retardation and some of them can be fatal. While *H.influenzae* causes only about 30% of all otitis media, it is the most frequent cause of recurrent otitis media. Loss of hearing (and its accompanying retardation in learning) increases with the number of otitis episodes. Adult diseases are principally mucosal and include chronic bronchitis, sinusitis and pneumonia. *H.influenzae* is increasingly recognized as an important pathogen in adult and elderly populations.

Mucosal *H.influenzae* diseases are mainly caused by non-type b encapsulated and non-encapsulated ($NT_b H.influenzae$) strains of the organism and invasive *H.influenzae* diseases are almost exclusively caused by type b encapsulated strains (*H.influenzae* b). No vaccine exists for $NT_b$ *H.influenzae* disease. A Type b capsular polysaccharide vaccine is available. The vaccine consisting of purified polyribitol phosphate (PRP), is partially effective but has several serious disadvantages. It is not antigenic or effective in the most susceptible group, that is children under the age of 18 months, and it is not completely effective in older children or in all populations. A new version of this vaccine has been recently licensed in which the polysaccharide is combined with a protein to enhance the polysaccharide's antigenicity. The conjugate vaccine appears more effective in younger populations. Neither of these vaccines gives any protection against mucosal *H. influenzae* diseases and neither of them prevents transmission of *H.influenzae* infection or colonization of the human nasopharynx.

We have discovered four morpholological and adhesion classes of pili on *H.influenzae* clinical isolates from different diseases, anatomical sites, ethnic groups and geographical areas. The principal pilus class, termed LKP pili, has been characterized in detail and evaluated as a purified pilus vaccine in a valid animal model of *H.influenzae* disease. LKP pili adhere to human erythrocytes, as do many of the pili used in other vaccines. Both $NT_b$ *H.influenzae* and *H.influenzae* b strains can express LKP pili of the same serotypes, opening the possibility that one purified LKP pilus vaccine consisting of mixed serotypes can protect against several *H.influenzae* diseases. Although at least eight different serotypes of LKP pili have been found, only a restricted number of them occur frequently on clinical isolates.

Purified LKP pilus vaccines have been tested in the chinchilla model of otitis media. A single pilus vaccine was safe, antigenic, and protected against both nasopharyngeal colonization and middle ear disease. Excellent protection was obtained irrespective of whether inoculation of the bacteria was directly into the middle ear or into the nasopharynx, and whether inoculation was with the piliated phase of the nonpiliated phase of *H.influenzae* bacteria. When inoculation was with the non-piliated phase, a rapid shift to the piliated phase occurred in the nasopharynges and middle ears of the animals. This observation is consistent with an important role for LKP pili in colonization and virulence. Pilus vaccine immunization completely eliminated piliated phase bacteria from both anatomical sites. Protection was shown to be LKP pilus type specific.

BRIEF DESCRIPTION OF THE DRAWINGS

FIG. I is a graph of proportion of positive cultures against time after nasal instillation and barotrauma of *Hemophilus influenzae* into the bullae showing protection against bullar colonization in chinchillas by LKP pilus vaccine immunization. Intrabullar challenge.

FIG. II is a graph of proportion of otitis media disease signs (middle ear effusion) against time after inoculation of *Hemophilus influenzae* into the bullae showing protection against otitis media in chinchillas by LKP pilus vaccine immunization. Intrabullar challenge.

Figure 1:
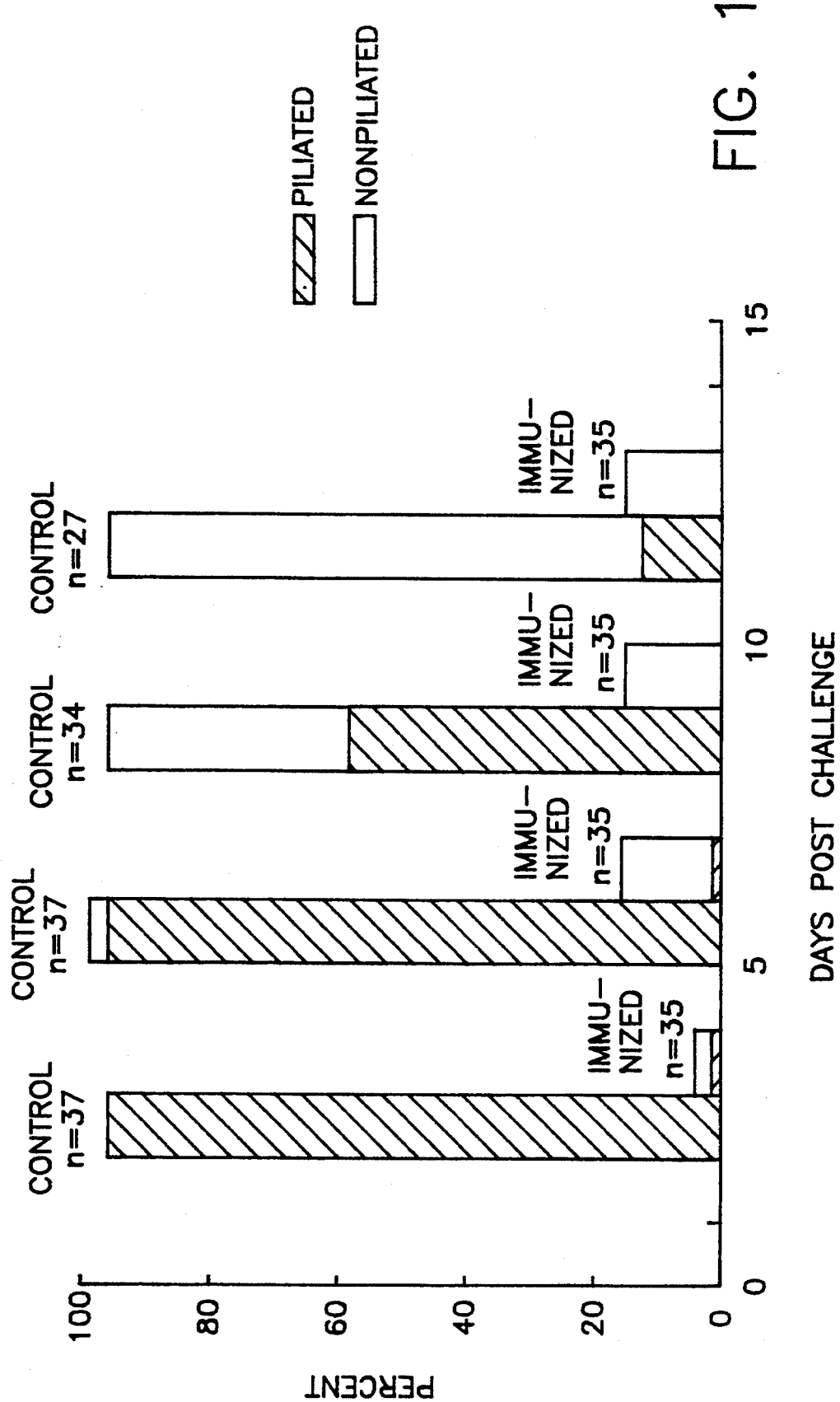
Figure 2:
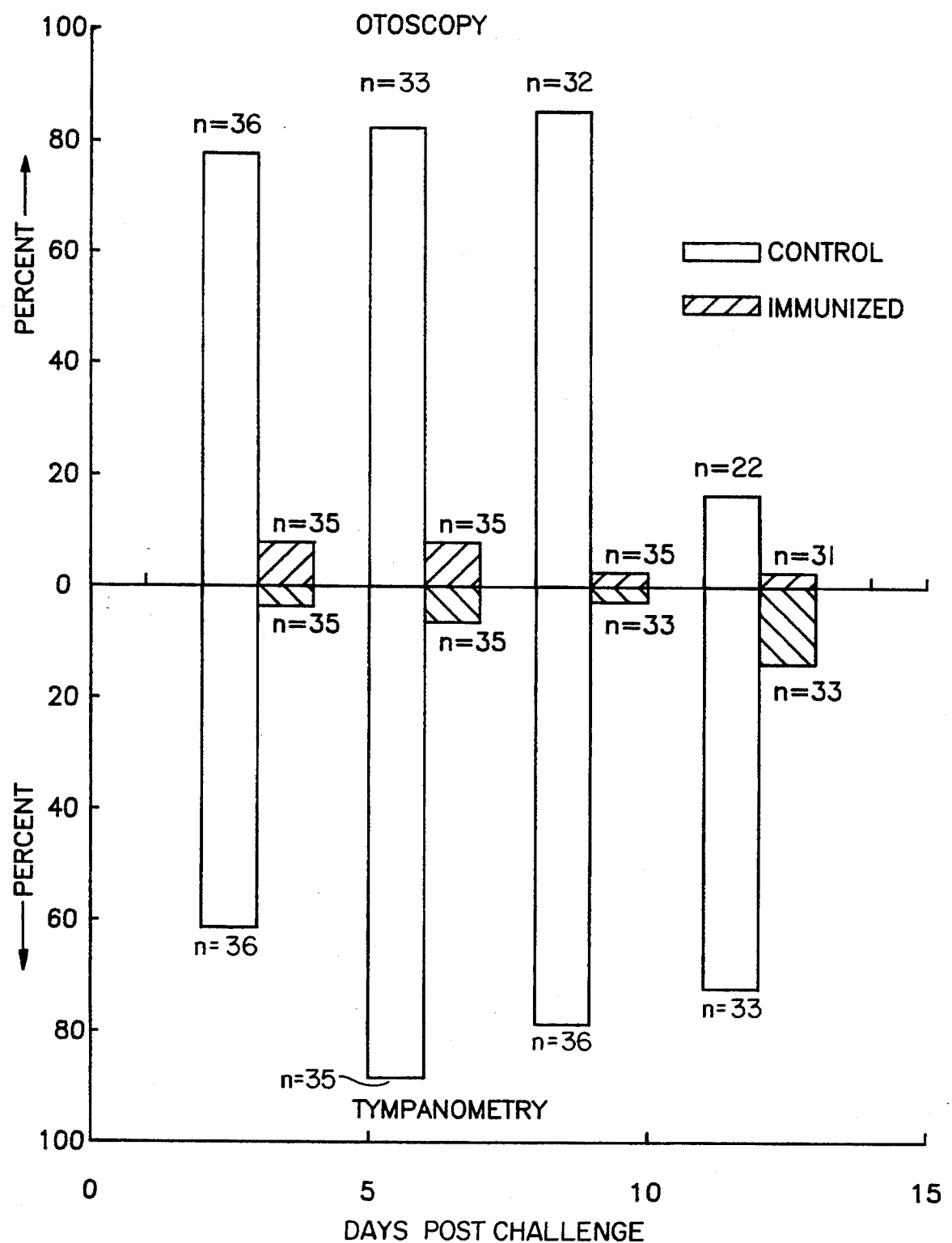
Figure 3:
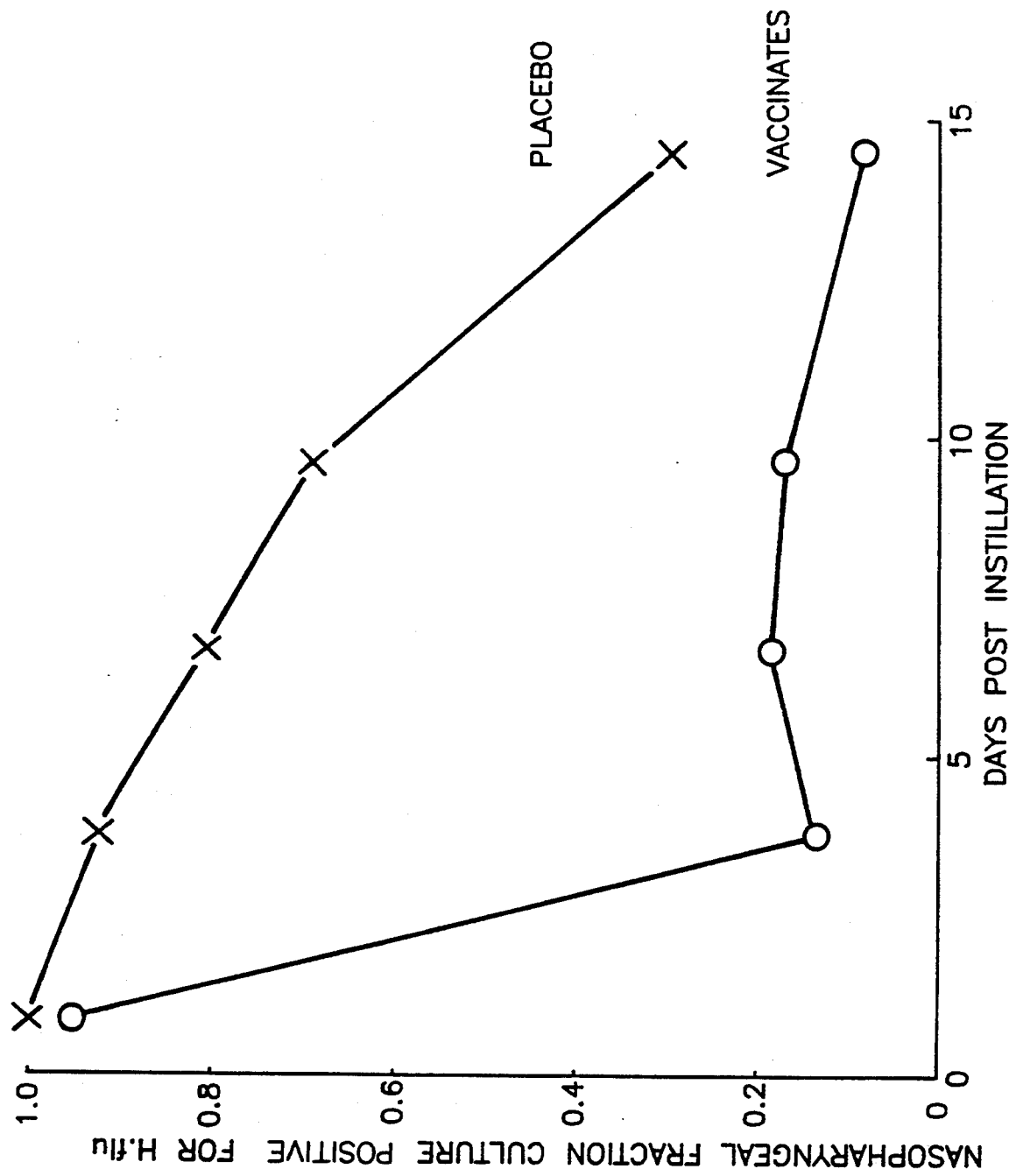

FIG. III is a graph of proportion of positive cultures against time after instillation of *Hemophilus influenzae* nasal colonization in chinchillas protected by LKP pilus vaccine immunization. Nasopharyngeal/barotrauma challenge.

FIG. IV is a graph of proportion of positive cultures against time after instillation of *Hemophilus influenzae* bullar colonization in chinchillas protected by LKP pilus vaccine immunization. Nasopharyngeal/barotrauma challenge.

DESCRIPTION OF THE PREFERRED EMBODIMENTS

The following LKP strains of *H. influenzae*, deposited at the American Type Culture Collection, 12301 Parklawn Drive, Rockville, Md. 20852, on Jun. 15, 1988 are identified by LKP pilus type; Applicants' reference number and ATCC designation:

LKP type 1 pilus-86-0295-ATCC 53775
LKP type 2 pilus-81-0568-ATCC 53776
LKP type 3 pilus-KL/8434-1-ATCC 53777
LKP type 4 pilus-86-1249-ATCC 53778
LKP type 5 pilus-81-0384-ATCC 53779
LKP type 6 pilus-86-0612-ATCC 53780
LKP type 7 pilus-87-0297-ATCC 53781
LKP type 8 pilus-FIN 48-ATCC 53782

The pili may be administered orally—say, in capsule form—or by injection—that is to say, subcutaneous, intradermal, or intramuscular injections. Where the mode of administration is by injection, since the pili may be insoluble, any pharmaceutically acceptable suspending medium may be employed. It has been found especially useful to employ phosphate buffer, suitably containing merthiolate, as the vehicle or suspending medium. It is preferred to use 0.0005–0.1, most suitably 0.0004M phosphate buffer, at ionic strength containing 0.0005 to 0.1 u, and, suitably 0.01% merthiolate. The concentration of pili in the vehicle is not critical. The sole criterion of desirability being that the pili shall be sufficiently finely divided to provide a suspension which meets generally accepted standards of syringeability. A concentration of 1–30, preferably about 20 mg. of pilus protein per 10 ml. of suspending medium is especially suitable.

It is generally preferred to administer the vaccine composition in more than one dose separated by a predetermined time interval. This time interval is selected to permit the formation of an adequate titer of antibodies to the pili in the injected subject.

Since there are no local or systemic toxic effects engendered by the injection of vaccine, there appear to be no upper limits to the dosage administered. It has been found suitable, however, to administer between 1 and 100 micrograms of pili per kilogram of body weight, most suitably about 20 micrograms per kilogram of body weight per injection.

The foregoing amounts refer to total pilus protection. Thus, if 10 pilus types from each of the designated strains are used in a mixture, a certain measure of protection is provided by a vaccine containing at least one member of each pilus type.

In vivo testing by Intrabullar and Nasal challenge Barotrauma Bacterial Isolates and Cultures A non-typable *H.influenzae* strain 86-0295 isolated from the middle ear of a child with acute otitis media were used in these experiments. Bacteria was grown overnight on Brain Heart Infusion Agar (DIFCO) supplemented with 10 ug. each of NAD (SIgma, N7004) and Hemin (Sigma H2250) (S-HBIA - Formula II) at 37° C. with 80% relative humidity and 5% $CO_2$. The original isolate contained no detectable (by hemagglutination and by Electron Microscopy) piliation and piliated phase bacteria were selected by hemasbsorption (A Hemabsorption Method for Detection of Colonies of Haemophilus Influenzae Type b Expressing Fimbriae, Connor. E.M. and M.R. Loeb, *Journal of Infectious Diseases*, Vol. 148, pp. 855-860 (1983) (incorporated herein by reference). Aliquots of piliated (P+) and non-piliated (P-) strain 86-0295 were stored at -70° C. using 5.5% Dimethyl Sulfoxide (DMSO) in Tryptic Soy Broth (TSB) as cryo protectant.

Vaccine Preparation

Pilus vaccine was prepared from P+ 86-0295 grown on S-BHIA in aluminum cookie trays by methods set forth below in Examples I thru III.

Experimental Animals and Vaccination

Adult chinchillas obtained from local ranges and exmained by otoscopy and tympanometry to be free of prior ear diseases were used in the experiment. Each animal was identified by a number on a neck collar and on the external ear. A code assigning each animal as to vaccine or placebo was developed and kept by an uninterested colleague until all experimental observations were completed. One-half of the animals were assigned to the placebo (Phosphate Buffered Saline-PBS) group and the other half animals to the vaccine group. Each dose consisted of 0.5 ml. of the vaccine or the placebo contained in a syringe labeled only with the animal's identification number. Each animal was given 2 intramuscular injections 28 days apart.

Serological Assays

Immediately before the first immunization, 10 days after the booster injection and 14 days after barotrauma, 1 ml. of blood was taken from the heart of each animal. Serum samples were prepared by standard methods and antipilus antibody titers were determined by piliated bacteria agglutination assay (PBAA).

Overnight grown P+ 86-0295 bacteria were harvested into formalinized (0.5%) PBS for use as stock test antigen (STA). Working test antigen was prepared by diluting with PBS from STA to a standardized concentration of 0.5 optical density (OD) units as determined in a 13 mm. glass tube at 540 nm. 50 ul. aliquots of the test serum were two-fold serially diluted in PBS in a 96-well flat bottom micro titer plate. The diluted serum was mixed with 50 ul. of the standardized test antigen and the test plate shaken at 150 rpm at room temperature for 20 minutes. The reactions were observed under a 20×stereomicroscope. The titer of a test serum is defined as the reciprocal of the dilution factor under which a distinct bacterial agglutination can be observed.

Experimental Infection 10 days following the booster injection, each group of animals was randomly divided into two subgroups, equal in number by the vaccine code keeper. One subgroup of animals was infected with the P+ bacteria and the other P- bacteria.

10 ml. of Brain Heart Infusion broth supplemented with 10 ul. each of NAD and Hemin in a 15×160 mm. tube was inoculated with 20 ul. of either a P+ or a P- suspension. The liquid cultures were incubated unshaken at 37° C. with 5% $CO_2$ and 80% relative humidity for about 17 hours. Such cultures routinely attained approximately $1 \times 10^9$ colony forming units (cfu) per ml. Immediately before use, the cultures were diluted 1:10 with sterile saline.

Before infection, each animal was examined for prior middle ear infection. 0.1 ml. of the appropriate bacterial suspension was inoculated into the bulla through a small hole pierced in the bony covering of the bulla. The hole was then covered with tape. Samples of the bullar contents were removed subsequently through the same hole. The challenge dose was 10 colony-forming units per ml.

Nasal/Barotrauma Challenge 0.5 ml. of the appropriate bacterial suspension was delivered to the right naris using a 18 gauge catheter tube. The challenge dose was $10^8$ colony forming units/ml.

One day following nasal infection, nasal samples were collected on a chocolate agar plate from each animal by transnasal instillation of saline. Then, each animal was placed under barotrauma by placement of a needle into the epitympanic bulla and application of 25 mm Hg of negative pressure for 5 minutes. After barotrauma, the animals were returned to their cages.

Culture and Clinical Observations

Samples for culture and clinical observations were made 3, 6, 9 and 14 days following challenge according to Table 1 below:

TABLE 1

| Day Following Barotrauma | Clinical Observation (bilateral) | | Sample for Culture | Bullar | |
|---|---|---|---|---|---|
| | Otoscopy | Tympanometry | Nasal | Left | Right |
| 3 | + | + | + | + | − |
| 6 | + | + | + | + | − |
| 9 | + | + | + | + | + |
| 14 | + | + | + | + | + |

The results of the intrabullar challenge are illustrated in FIGS. I and II. FIG. I data show that colonization of the chinchilla middle ear (bulla) can be effectively prevented by immunization with purified LKP pili. FIG. II data show that the disease signs of otitis media can be effectively prevented by immunization with purified LKP pili.

Serum Antibody Titers

Following primary and booster vaccination with the purified LKP pilus vaccine, 6 originally had no rise in piliated cell agglutination titer, 14 had titers in the 2 to 16 range, 10 had titers in the 17 to 64 range and 5 had titers of greater than 100. No non-immunized animal had a detectable titer.

The results of the nasopharyngeal barotrauma challenge are illustrated in FIG. III. FIG. III data show that pilus immunization protects when the route of infection is the natural one via the nasopharynx. Large inocula ($10^8$ colony-forming units) of bacteria are necessary to infect by this route. However, pilus immunization is highly effective in spite of the large challenge dose. Pilus immunization protected equally well whether the inoculation was in the pilated or nonpiliated phase. The nonpiliated inoculum rapidly shifted to the piliated phase in the nasopharynx in non-immunized animals. FIG. IV data show that the rapid elimination of *H.influenzae* bacteria from the nasopharynx of pilus-immunized chinchillas. The significance of this result is great. The reservoir of *H.influenzae* bacteria causing disease is the human nasopharynx/throat (upper respiratory tract). *H.influenzae* infection is transmitted from one human respiratory tract to another. The *H.influenzae* bacteria that cause disease in an individual originate in that individual's upper respiratory tract. If pilus immunization can prevent transmission to and colonization of the upper respiratory tract, widespread use of a pilus vaccine could eradicate *H.influenzae* as a pathogen. Thus, our vaccine may provide epidemiological as well as individual disease control, and eventually eradicate *H.influenzae* disease.

Passive Immunization

Bacterial Isolates and Cultures

Same as NP-Barotrauma Experiment above.

Antiserum Preparation

Vaccines prepared by methods detailed (in NP-Barotrauma experiment) previously. Matured young New Zealand rabbits were immunized subcutaneously with 200 ug. pilus protein mixed with Freund's incomplete adjuvent. 3 injections were given at 4-week intervals. After the last booster, animals were bled through the marginal ear vein and serum prepared by standard methods. The serum was titrated for antipilus antibodies using piliated bacteria agglutination as detailed previously. The preparation used in this experiment had an agglutination titer of 10,240.

Experimental Animals, Immunization and Challenge 40 adult chinchillas were obtained from local ranches. Before immunization, each was examined for prior middle ear infection by otoscopy and tympanometry. The animals were divided into 4 groups of 10 animals each, using a blind code. Code syringes containing 1 ml. of eitehr undiluted hyperimmune antipilus serum, 1 ml. of 1:10 diluted antipilus serum, 1 ml. of 1:100 diluted antipilus serum, or 1 ml. of non-immune serum. Each animal was given its coded injection intraperitoneally. One day following immunization, each animal was challenged into the right bulla with 10 cfu of piliated 86-0295.

Culture and Clinical Observations

Four and 8 days following bullar challenge, each animal was clinically observed by otoscopy and tympanometry. Samples for culture were taken through a surgically opened bullar by an alginate swab. Samples were streaked onto chocolate agar plates and incubated overnight at 37° C. with 5% $CO_2$ and 80% relative humidity. Individual isolated colonies were picked using sterile filter paper strips and resuspended in a drop of PBS on a ring slide. A drop of appropriately diluted antipilus serum was added and the slide shaken (150 rpm) at room temperature for 15 minutes. Positive agglutination indicates the colony contained piliated bacteria.

The results are shown in Table 4. Table 4 shows that protection against *H. influenzae* colonization and otitis media disease can also be obtained when LKP pilus antibodies are administered passively. The antibodies may be produced in a different species than the one protected. This result is important because patients at high risk of disease or with an overwhelming *H. influenzae* infection could be given immediate protection by the injection of LKP pilus antibodies as a passive immunoprophylactic or as an immunotherapeutic.

TABLE 2

Protection of Chinchillas Against Experimental Otitis Media by The Passive Administration of Homologous Antipilus Rabbit Serum intrabullar Challenge with 10 Colony-Forming Units.

| Antibody Dosage Group | Relative[2] Serum Dilution | Fraction[3] with Circulating Antibody | Geometric Mean Agglutination Titer | Fraction[4] Infected at 4 Days | Percent Protection Against Infection | Fraction[5] Symptomatic at 4 Days | Percent Protection Against Symptoms | Fraction[6] with Piliated Phase at 4 Days |
|---|---|---|---|---|---|---|---|---|
| High | 1 | 8/9[1] | 95 | ⅜ | 63% | ⅜ | 63% | ⅛[1] |
| Medium | 1/10 | 8/8 | 99 | ⅜ | 63% | ⅛ | 88% | 0/8 |
| Low | 1/100 | 7/7 | 7 | 2/7 | 86% | 3/7 | 57% | 0/7 |
| Control | 0 | 0/10 | 0 | 10/10 | 0% | 10/10 | 0% | 10/10 |

[1] The single animal infected with piliated phase cells was also the single animal with no circulating antibody.
[2] Animals injected IP with 1 ml serum; undiluted titer = 20,480.
[3] Animals bled at time of challenge.
[4] Determined by bullar culture.
[5] Determined by direct observation of bulla.
[6] Piliated phase bacteria determined by antiserum agglutination.

The following is a description of the general growth and purification procedures that were found to give acceptable yield and purity of protein. Exceptions to the general procedure are noted.

EXAMPLE I

General Outline of Purification of *H. influenzae* Pili. Inoculum Preparation, Growth and Harvest Frozen p+ seed cultures of *H. Influenza* CHP 86-1249b were thawed and plated on supplemented brain-heart infusion agar. Plating was performed 18-20 hours before the anticipated tray inoculatin. The plates were incubated at 37° C., with 80% relative humidity and 5% $CO_2$. The percentage of the colonies having hemagglutinating activity was assessed. Generally, ten individual colonies were picked and assayed. In all cases at least nine out of 10 colonies were HA+ for human red cells.

Trays of GC base supplemented with DSF and hemin were inoculated with bacteria suspended in a culture transfer solution. The transfer solution was a potassium phosphate buffered saline solution containing 5mg/ml. beta-NAD. Bacteria were scraped from the plates with dacron swabs and suspended in the transfer solution until visibly turbid. Each tray was then inoculated with 2.5 ml. A glass spreader was used to distribute the inoculum evenly over the surface of the medium. Inoculated trays were incubated for 20 hours at 37° C. with 5% $CO_2$ and 80% relative humidity.

Growth was scraped from the agar using a metal scraper and 5-10 ml. of harvest buffer per tray. Since the cells were being washed before blending, the harvest buffer was at pH 5 to crystallize and recover any pili which had been shed.

EXAMPLE II

Blending and Initial Stages of Cycling

Each cell pellet from Example I, was resuspended in a volume of blending buffer such that the suspension volume was 150-200 ml., or about 5 ml. of buffer per gram of wet cell pellet. The pellet was not completely resuspended but instead broken up sufficiently so that it could be removed from the centrifuge bottle. Blending was performed using the large cup and unmodified blade assembly of the Omni mixer. Each resuspended pellet was blended for 3 minutes at a speed of 10-11 k rpm. After blending, "depiliated" cells were removed by centrifugation at $15,300 \times g$. for 20 minutes. The supernatant was poured off and further clarified by another centrifugation at $15,300 \times g$. for 20 minutes. The supernatant was poured off and the cell pellets discarded.

The first crystallization was performed by dialysis of the crude supernatant against a pH 5 acetate buffer. Dialysis was performed against 20 volumes of buffer overnight at 4° C. Dialysis was performed against 20 volumes overnight at 4° C. Crystalline pili, appearing as large chunky aggregates in the darkfield, were sedimented for 60 minutes at 4° C. and $22,100 \times g$. The supernatant was poured off and discarded. The pellets were inverted over paper towels to drain briefly. This point marked the end of the first cycle.

Solubilization of the pellets was performed by resuspension in 0.01M caps buffer, at half the original crude volume. The pellets were broken up by the use of a rubber policeman and by drawing the pellets into and out of a 10 ml. pipette. The pellets, brown in color, were then allowed to solubilize at 4° C. with no stirring for several hours or overnight. The preparation was clarified by centrifugation at 22,100 x g for 60 minutes. The preparation was loaded into dialysis tubing then dialyzed against 50 mM sodium acetate buffer pH 5. Dialysis was performed in the cold overnight. Pilus aggregates were then collected and centrifugation of dialysis to the content. This point marked the end of the second cycle.

The third cycle was identical to the second, except that the volume of solubilizing buffer used was half of that used in the second cycle.

EXAMPLE III

Final Stages of Cycling

After 3 cycles, the preparation still carried a faint yellow color, although it seemed fairly clean by SDS-PAGE. The following cycles were performed to remove additional impurities.

Crystalline pili were sedimented by centrifugation at $22,100 \times g$. Pili were solubilized in a pH 10.5 phosphate buffer containing 5 m. M EDTA and 0.2% Triton X-100 (PBET). The same volume as in the previous cycle was used. Solubilization was performed at 4° C. with occasional mild stirring and was usually completed within 4 hours. Clarification was performed by centrifugation at $22,100 \times g$ for 60 minutes. The supernatant was carefully poured off, leaving a clear gelatinous pellet.

Sodium chloride and polyethylene glycol were used as the crystallizing agent in the 4th cycle. However, to facilitate crystallization, it was necessary to first lower the pH from 10.5 to 7.5-8.0 by titration with HCl. The pili, still soluble at this stage, were crystallized by adding 5M sodium chloride to a final concentration of 0.5M and 30% PEG to a 3% final concentration. Streaming birefringence was visible immediately. The preparation was held at 4° C. for 1 hour and then the crystalline pili sedimented by centrifugation at $22,100 \times g$ for 60 minutes. This point marked the end of the 4th cycle.

The yellow supernatant was poured off and discarded and the pellets inverted to drain. Solubilization was performed again in the PBET, followed by clarification by centrifugation at $22,100 \times g$ for 60 minutes. Again, after removal of the supernatant, a clear gelatinous pellet remained. This point marked the end of the 5th cycle.

The 6th cycle was identical to the 5th, except that the pH 10.5 phosphate buffer used for solubilization did not contain EDTA or Triton X-100.

The preparation is stored soluble, in the final pH 10.5 phosphate buffer, with 0.02% sodium azide as a preservative.

EXAMPLE IV

In accordance with the procedures of Examples I thru III, but in place of strain CHP 86-1249, there were prepared all of the pili of the strains set forth in Table 3. Slight variations in solubility may occur. For example, LKP3 pili are less soluble at pH 6 than at pH 5. Also, LKP2 pili are less soluble at pH 4 than pH 5. However, all 8 types can be purified using the described procedure.

The following formulas were used in all of the foregoing standard preparations.

FORMULA I

Hemin Stock 10 mg.ml.

Hemin is dissolved at a concentration of 10 mg./ml. in 0.05N NaOH. The hemin is usually autoclaved to sterilize, but filter sterilization through a 0.2u. filter is possible if care is taken to thoroughly dissolve the hemin. The stock may be stored at 4° C. for up to 1 week or at −20° C. indefinitely.

(For 40 trays: 0.6 gm. hemin in 60 ml. 0.05N NaOH)

FORMULA II

NAD Stock 5 mg./ml.

Beta-nicotinamide adenine dinucleotide is dissolved in a potassium phosphate buffered saline solution. The lab standard 20×$k_2$/$KH_2PO_4$ media stock solution is diluted 1:20 with 0.85% NaCl to make the appropriate volume of buffer. The NAD is dissolved and then filter sterilized through a 0.2 u. filter. The stock may be stored at 4° C. for up to 1 month or frozen at −20° C. indefinitely.

FORMULA III

Hemin-NAD Stock for Plate Media

Combine 1 part sterile Hemin Stock with 2 parts sterile NAD Stock. Dispense into freezing vials, 3.5 ml. per vial. Store frozen at −20° C. To use, thaw and add 3 ml./liter of sterile medium at no higher than 52° C. The medium will be 10 ug./ml. hemin, 10 ug./ml. NAD.

FORMULA IV

Supplemented Brain-Heart Infusion Agar (S-BHIA)

To a 2-liter flask, add:
1 stir bar
37 gm. DIFCO brain-heart infusion
20 gm. DIFCO Bacto agar
1 L $dH_2O$ Autoclave 25 minutes to sterilize. Cool to 50°–52° C. With stirring, add 3 ml. of Hemin-NAD stock. Pour.

FORMULA V

DSF Supplement

| Dextrose | 600 gm. |
| --- | --- |
| 1-Glutamine | 15 gm. |
| Ferric Nitrate | 0.75 gm. |
| $dH_2O$ | 1.5 L. |

Dissolve by stirring with mild heating. Dispense into 1 liter bottles, 500 ml./bottle. Autoclave 20 minutes to sterilize. Store at 42° C.

FORMULA VI

GC Tray Medium

For each 4.0 L flask or 4 trays:
90 gm. DIFCO GC Base
2.5 L $dH_2O$
Autoclave 40 minutes to sterilize.
Add 25 ml. DSF supplement and 5 ml. sterile Hemin Stock, 10 mg./ml. Swirl to mix, then pour. This medium should contain approximately 20 ug./ml. Hemin.

FORMULA VII

| Harvest Buffer — PBS, 0.15 u., pH 5.0 | |
| --- | --- |
| Sodium phosphate, monobasic monohydrate | 5.6 gm. |
| Sodium chloride | 3.2 gm. |
| $dH_2O$ | 800 ml. |

Adjust pH to 5.0, then bring to 1 L with $dH_2O$.

FORMULA VIII

| Blending Buffer — TBS, pH 10–10.3 | |
| --- | --- |
| TRIS | 12.1 gm. |
| Sodium Chloride | 8.5 gm. |

Adjust pH to 10–10.3, then bring to 1 L with $dH_2O$.

FORMULA IX

| Dialysis Buffer — M Acetate Buffer | |
| --- | --- |
| Sodium Acetate, Anhydrous | 17.23 gm. |
| Glacial Acetic Acid | 5.14 ml. |
| $d.H_2O$ | 5 L |

Adjust pH to 5.0 with acetic acid, then bring to 6 L with $d.H_2O$ (distilled $H_2O$).

FORMULA X

| Solubilizing Buffer — 0.01M CAPS, pH 10.4 | |
| --- | --- |
| CAPS (3-[cyclohexylaminol]-1-propane sulfonic acid) | 2.21 gm. |
| $dH_2O$ | 800 ml. |

Adjust pH to 10.4 with NaOH, then bring to 1 L with $dH_2O$.

FORMULA XI

| Solubilizing Buffer — 0.1 u. Phosphate Buffer + 5m M EDTA +0.2% Triton X-100 (PBET). | |
| --- | --- |
| Sodium phosphate dibasic | 7.92 gm. |
| Tertiary sodium phosphate ·12$H_2O$ | 0.08 gm. |
| Disodium ethylene-diaminetetraacetate | 1.86 gm. |
| Triton X-100 | 2 ml. |
| $dH_2O$ | 800 ml. |

Titrate to pH 10.3–10.5 with NaOH. Bring to 1 L with $dH_2O$.

FORMULA XII

| Solubilizing Buffer — 0.1 u. Phosphate Buffer | |
| --- | --- |
| Sodium phosphate dibasic | 7.92 gm. |
| Tertiary sodium phosphate.12$H_2O$ | 0.08 gm. |
| $dH_2O$ | 800 ml. |

Titrate to pH 10.3–10.5. Bring to 1 L with $dH_2O$.

FORMULA XIII

5M Sodium Chloride

| Sodium Chloride | 292.2 gm. |
| --- | --- |
| $dH_2O$ | 1 L |

Filter through a 0.45 u. filter to sterilize.

FORMULA XIV

| Polyethylene Glycol, 30% | |
|---|---|
| PEG-8000 (Fisher Carbowax) | 300 gm. |
| dH$_2$O | 700 ml. |

Filter through a 0.45 u. filter to sterilize.

TABLE 3

FREQUENCY OF LKP PILUS TYPES ON INDEPENDENT CLINICAL ISOLATES OF HAEMOPHILUS INFLUENZAE

| Pilus Type | Strain/Capsule | Disease Source* | LKP1 (86-0295) | LKP2 (81-0568) | LKP3 (Eagan) | LKP4 (86-1249) | LKP5 (81-0384) | LKP6 (86-0612) | LKP7 (87-0297) | LKP8 (FIN 48) | (LKP) HA+# | (EM) P+@ |
|---|---|---|---|---|---|---|---|---|---|---|---|---|
| LKP1 (86-0295) | | | | | | | | | | | | |
| | CB/86-0295/nt | OM | + | | | | | | | | + | + |
| | JR/Henderson/b | NP | + | | | | | | | | + | + |
| | KL/8418-1/b | epigl | + | | | | | | | | + | + |
| | KL/8430-1/b | men | + | | | | | | | | + | + |
| LKP2 (81-0568) | | | | | | | | | | | | |
| | CB/81-0568/e | OM | | + | | | | | | | + | + |
| | CB/85-0911/e | OM | | + | | | | | | | + | + |
| | CB/86-0779/e | OM | | + | | | | | | | + | + |
| | CB/86-1067/e | OM | | + | | | | | | | + | + |
| | CB/86-1454/nt | OM | | + | | | | | | | + | + |
| | CB/87-0199/e | OM | | + | | | | | | | + | + |
| LKP3 (Eagan) | | | | | | | | | | | | |
| | JR/Eagan/b | men | | | + | | | | | | + | + |
| | JR/1147/b | epigl | | | + | | | | | | + | + |
| | JR/Madigan/b | men | | | + | | | | | | + | + |
| | KL/8434-1/b | epigl< | | | + | | | | | | + | + |
| | KL/8440-1/b | epigl | | | + | | | | | | + | + |
| LKP4 (86-1249) | | | | | | | | | | | | |
| | CB/86-1249/nt | OM | | | | + | | | | | + | + |
| | KL/8405-1/b | men | | | | + | | | | | + | + |
| | KL/8408/b | PC | | | | + | | | | | + | + |
| | KL/8410-1/b | men | | | | + | | | | | + | + |
| | KL/8411-1/b | SA | | | | + | | | | | + | + |
| | KL/8414-1/b | BC | | | | + | | | | | + | + |
| | KL/8415-1/b | SA | | | | + | | | | | + | + |
| | KL/8417-1/b | men | | | | + | | | | | + | + |
| | KL/8419-1/b | BC | | | | + | | | | | + | + |
| | KL/8420-1/b | men | | | | + | | | | | + | + |
| | KL/8429/b | men | | | | + | | | | | + | + |
| | KL/8433/b | men | | | | + | | | | | + | + |
| | KL/8436-1/b | men | | | | + | | | | | + | + |
| | KL/8448-1/b | men | | | | + | | | | | + | + |
| | KL/8453/b | men | | | | + | | | | | + | + |
| | KL/8501-1/b | men | | | | + | | | | | + | + |
| | KL/8502-1/b | men | | | | + | | | | | + | + |
| | KL/8503-1/b | men | | | | + | | | | | + | + |
| | KL/8504-1/b | epigl | | | | + | | | | | + | + |
| | KL/8505-1/b | men | | | | + | | | | | + | |
| | KL/8507-1/b | men | | | | + | | | | | + | + |
| LKP4 (86-1249) | | | | | | | | | | | | |
| | EH/AT102/b | | | | | + | | | | | + | |
| | EH/CH100/b | | | | | + | | | | | + | |
| | EH/COL-NY10/b | | | | | + | | | | | + | |
| | EH/DV102/b | | | | | + | | | | | + | |
| | EH/NA100/b | | | | | + | | | | | + | |
| | EH/NO100/b | | | | | + | | | | | + | |
| | EH/NO105/b, | | | | | + | | | | | + | |
| | EH/DL42/b | | | | | + | | | | | + | |
| | EH/DL166/b | | | | | + | | | | | + | |
| | EH/OC104/b | | | | | + | | | | | + | |
| | RM/P2047/b | SA | | | | + | | | | | + | |
| | RM/SP1468/b | men | | | | + | | | | | + | |
| | RM/B536/b | men | | | | + | | | | | + | |
| | RM/B5379/b | BC | | | | + | | | | | + | |
| | RM/P4488/b | SA | | | | + | | | | | + | |
| | RM/B2917/b | SA | | | | + | | | | | + | |
| | RM/B3813/b | men | | | | + | | | | | + | |
| | RM/B1565/b | men | | | | + | | | | | + | |
| | RW/82 | men | | | | + | | | | | + | |
| | RW/< | men | | | | + | | | | | | |

TABLE 3-continued

FREQUENCY OF LKP PILUS TYPES ON INDEPENDENT CLINICAL ISOLATES OF HAEMOPHILUS INFLUENZAE

| Pilus Type | Strain/Capsule | Disease Source* | Purified Pilus Typing Serum (Rabbit, Unabsorbed) | | | | | | | | (LKP) HA+ # | (EM) P+ @ |
|---|---|---|---|---|---|---|---|---|---|---|---|---|
| | | | LKP1 (86-0295) | LKP2 (81-0568) | LKP3 (Eagan) | LKP4 (86-1249) | LKP5 (81-0384) | LKP6 (86-0612) | LKP7 (87-0297) | LKP8 (FIN 48) | | |
| LKP5 (81-0384) | | | | | | | | | | | + | + |
| | CB/81-0384/nt | OM | | | | | + | | | | + | + |
| | CB/86-1814/nt | OM | | | | | + | | | | + | + |
| | CB/87-0944/nt | OM | | | | | + | | | | + | + |
| | KL/8458-1/b | SA | | | | | + | | | | | |
| LKP6 (86-0612) | | | | | | | | | | | + | + |
| | CB/86-0612/f | OM | | | | | | + | | | + | + |
| | CB/88-0349/nt | Thr | | | | | | + | | | + | + |
| LKP7 (87-0297) | | | | | | | | | | | | |
| | CB/87-0297/f | OM | | | | | | | + | | | |
| LKP8 (FIN 48) | | | | | | | | | | + | | |
| | FIN 48 | OM | | | | | | | | | | |

NOTE:
*OM, otitis media; NP, nasopharyngeal; epigl., epiglottitis; men, meningitis PC, periorbital cellulitis; SA, septic arthritis; BC, buccal cellutitis.
Hemagglutination of human erythrocytes.
@ LKP piliation by electron microscopy.

Reverse Phase HPLC Amino Acid Compositions and Molecular Weights of Eight Hemophilus influenzae LKP Pilus Preparations

| Amino acid ($n_j$) | Strain and/or Preparation | | | | | | | |
|---|---|---|---|---|---|---|---|---|
| | 86-0295 Lot 001 LKP1 | 86-0295 LKP1 | 86-0297 LKP1 | Eagan Lot 001 LP3 | 86-1249b LKP4 | 86-1067 Lot 001 LKP2 | 81-0384 LKP5 | Mix Lot 001 LKP1, LKP2, and LKP3 |
| Aspartic acid or Asparagine | 45.8 | 46.5 | 47.2 | 35.4 | 32.4 | 33.8 | 38.7 | 38.2 |
| Glutamic acid or Glutamine | 22.7 | 22.5 | 22.3 | 18.4 | 22.0 | 21.6 | 20.6 | 21.4 |
| Serine | 14.8 | 14.5 | 14.3 | 15.4 | 13.2 | 9.4 | 17.2 | 13.0 |
| Glycine | 16.2 | 15.6 | 15.5 | 16.6 | 16.8 | 19.3 | 22.1 | 17.8 |
| Histidine | 5.0 | 5.2 | 5.2 | 5.6 | 6.5 | 3.6 | 4.5 | 4.8 |
| Arginine | 2.7 | 2.3 | 2.3 | 1.1 | 4.5 | 8.5 | 5.8 | 4.4 |
| Threonine | 32.6 | 33.2 | 33.0 | 27.6 | 24.2 | 20.4 | 24.1 | 26.2 |
| Alanine | 23.3 | 23.5 | 23.4 | 17.7 | 17.7 | 22.0 | 24.1 | 21.3 |
| Proline | 5.3 | 5.3 | 4.3 | 3.7 | 6.5 | 4.0 | 6.4 | 3.7 |
| Tyrosine | 9.0 | 9.2 | 9.4 | 5.4 | 6.5 | 6.3 | 11.1 | 6.6 |
| Valine | 21.4 | 21.4 | 21.7 | 17.5 | 17.1 | 19.1 | 17.3 | 19.1 |
| Methionine | 2.0 | 2.0 | 1.8 | 1.8 | 3.3 | 0.8 | 1.8 | 1.8 |
| ½ Cystine | 2.1 | 2.5 | 2.1 | 1.7 | 1.8 | 2.1 | 2.1 | 2.0 |
| Isoleucine | 9.8 | 9.7 | 9.7 | 7.3 | 9.5 | 11.4 | 12.3 | 9.6 |
| Leucine | 9.9 | 9.7 | 9.4 | 15.4 | 14.9 | 14.6 | 13.9 | 13.9 |
| Phenylalanine | 8.7 | 8.5 | 8.6 | 9.5 | 8.5 | 4.3 | 7.1 | 7.3 |
| Tryptophan | 0.0 | 0.0 | 0.0 | 0.0 | 0.0 | 0.0 | 0.0 | 0.0 |
| Lysine | 18.8 | 18.3 | 19.7 | 16.8 | 16.6 | 16.0 | 15.7 | 16.9 |
| Total (N) | 250.1 | 249.9 | 249.9 | 216.9 | 222.0 | 217.2 | 244.8 | 228.0 |
| Daltons | 26934.3 | 26937.0 | 27001.0 | 23223.6 | 24105.9 | 23263.7 | 26168.8 | 24460.5 |
| μg/tube | 7.8 | 5.9 | 6.6 | 9.2 | 33.4 | 8.8 | 6.1 | 8.8 |

We claim:

1. A vaccine composition for protecting subjects against infections caused by piliated Haemophilus influenzae organisms which comprises a pharmaceutically acceptable carrier and whole H. influenzae pili, designated vaccine pili, previously separated from other H. influenzae components, in an amount which raises the antibody level of the subject to a level sufficient to provide protection, said vaccine comprising pili of at least one type selected from a group of pili types designated LKP1 through LKP8, said vaccine pili being agglutinable by anti sera derived from pili from at least one of the following organisms H. influenzae (86-0295) (ATCC 53775), LKP type 1 pilus;

H. influenzae (81-0568) (ATCC 53776), LKP type 2 pilus;

H. influenzae (KL/8434-1/B) (ATCC 53777), LKP type 3 pilus;

H. influenzae (86-1249) (ATCC 53778), LKP type 4 pilus;

H. influenzae (81-0384) (ATCC 53779), LKP type 5 pilus;

H. influenzae (86-0612) (ATCC 53780), LKP type 6 pilus;

H. influenzae (87-0297) (ATCC 53781), LKP type 7 pilus;

H. influenzae (FIN 48) (ATCC 53782), LKP type 8 pilus.

2. A vaccine of claim 1 comprising pili agglutinable by antisera derived from pili from organisms of at least (86-1249) (ATCC 53778).

3. A vaccine of claim 1 comprising pili agglutinable by antisera derived from pili from organisms of each of the strains named in claim 1.

4. A vaccine of claim 1 comprising pili derived from organisms of each of the strains named in claim 1.

5. A method of protecting subjects against infections caused by piliated *Haemophilus influenzae* organisms which comprises administering to a subject in need of protection a composition which raises the antibody level of the subject to a level sufficient to provide protection comprising:

whole *H. influenzae pili*, designated vaccine pili, previously separated from other *H. influenzae* components, said composition comprising vaccine pili of at least one type selected from a group of pili types designated LKP1 through LKP8, said vaccine pili being agglutinable by anti sera derived from pili from at least one of the following organisms

*H. influenzae* (86-0295) (ATCC 53775), LKP type 1 pilus;

*H. influenzae* (81-0568) (ATCC 53776), LKP type 2 pilus;

*H. influenzae* (KL/8434-1/B) (ATCC 53777), LKP type 3 pilus;

*H. influenzae* (86-1249) (ATCC 53778), LKP type 4 pilus;

*H. influenzae* (81-0384) (ATCC 53779), LKP type 5 pilus;

*H. influenzae* (86-0612) (ATCC 53780), LKP type 6 pilus;

*H. influenzae* (87-0297) (ATCC 53781), LKP type 7 pilus;

*H. influenzae* (FIN 48) (ATCC 53782), LKP type 8 pilus.

6. A method of claim 5 wherein the vaccine composition comprises pili agglutinable by antisera derived from pili from organisms of at least (86-1249) (ATCC 53778).

7. A method of claim 5 wherein the vaccine composition comprises pili agglutinable by anti sera derived from pili from organisms of each of the strains named in claim 5.

8. A method of claim 5 wherein the vaccine composition comprises pili derived from organisms of each of the strains named in claim 5.

* * * * *